United States Patent [19]

Wiese

[11] Patent Number: 5,496,368
[45] Date of Patent: Mar. 5, 1996

[54] TISSUE EXPANDER INFLATING DUE TO OSMOTIC DRIVING FORCES OF A SHAPED BODY OF HYDROGEL AND AN AQUEOUS SOLUTION

[76] Inventor: K. Günter Wiese, Heinz-Hilpert-Str. 12, D - 37085 Göttingen, Germany

[21] Appl. No.: 190,140

[22] PCT Filed: Jun. 12, 1993

[86] PCT No.: PCT/EP93/01490

§ 371 Date: Feb. 2, 1994

§ 102(e) Date: Feb. 2, 1994

[87] PCT Pub. No.: WO93/25266

PCT Pub. Date: Dec. 23, 1993

[30] Foreign Application Priority Data

Jun. 12, 1992 [DE] Germany .......................... 42 19 207.2

[51] Int. Cl.$^6$ ..................................................... A61F 2/12
[52] U.S. Cl. .................. 623/8; 623/11; 128/839; 606/191
[58] Field of Search .................. 623/8, 11; 606/191; 604/892.1; 128/839

[56] References Cited

U.S. PATENT DOCUMENTS

| | | | |
|---|---|---|---|
| 3,867,329 | 2/1975 | Halpern et al. | 260/29.6 H |
| 3,975,350 | 8/1976 | Hudgin et al. | 260/30.4 |
| 4,237,893 | 12/1980 | Michaels | 128/341 |
| 4,969,898 | 11/1990 | Calogero | 623/8 |
| 5,015,238 | 5/1991 | Solomon et al. | 604/164 |
| 5,074,878 | 12/1991 | Bark et al. | 623/8 |
| 5,076,965 | 11/1991 | Ersek et al. | 623/8 |
| 5,116,371 | 5/1992 | Christensen et al. | 623/11 |
| 5,192,326 | 3/1993 | Bao et al. | 623/11 |
| 5,207,706 | 5/1993 | Menaker | 604/266 |
| 5,246,454 | 9/1993 | Peterson | 623/8 |

FOREIGN PATENT DOCUMENTS

3540936C1  10/1986  Germany .

OTHER PUBLICATIONS

A Self–Inflating Tissue Expander, by Eric D. Austad, M.D., and Gregory L. Rose, *Plastic And Reconstructive Surgery*, vol. 70, 1982, pp. 588–594.

*Primary Examiner*—Paul B. Prebilic
*Attorney, Agent, or Firm*—Hopkins & Thomas

[57] ABSTRACT

A self-inflating tissue expander (1) serves to create cavities for the insertion of implants or to provide tissue for a self transplantation. The tissue expander itself is implanted into the tissue, where it absorbs body fluid, especially water from the surrounding tissue due to an osmotic driving force. The tissue expander (1) has a shaped body (5) made from hydrogel (2).

6 Claims, 2 Drawing Sheets

TISSUE EXPANDER INFLATING DUE TO OSMOTIC DRIVING FORCES OF A SHAPED BODY OF HYDROGEL AND AN AQUEOUS SOLUTION

FIELD OF THE INVENTION

The invention relates to a self-inflating tissue expander to create cavities for the insertion of implants or to provide tissue for a self transplantation, where the tissue expander itself is implanted in the tissue and where it absorbs body fluid, especially water from the surrounding tissue due to an osmotic driving force. In order to create cavities for the insertion of implants, but also to provide healthy tissue for a self transplantation, the method of controlled tissue expansion is applied. The tissue is continually stretched under a moderate application of pressure until the desired cavity or the desired amount of additional tissue is obtained.

BACKGROUND OF THE INVENTION

From the dissertation "Controlled Tissue-Expansion in Reconstructive Surgery" (Julian H. A. van Rappard, Thesis Groningen, The Netherlands, 1988) a tissue expander is known that is expanded by the gradual filling with a liquid. The tissue expander has an impermeable, stretch-resistant skin and a self-sealing valve for the filling with liquid using a hollow needle and a syringe. The tissue expander is implanted under the tissue to be expanded, with the valve arranged so that it is accessible by the needle from the outside. For the actual expansion of the tissue, the tissue expander is gradually filled with liquid. The needle is inserted into the valve through the tissue and the liquid is injected into the tissue expander with the syringe. When fully filled with liquid, the tissue expander obtains a shape determined by the form of its skin. The forming of the skin is adaptable to various applications in this way. It is an advantageous feature of the known tissue expander that a precisely controlled expansion of the tissue is possible. A major disadvantage, though, is the occurrence of high peak pressures after each filling of liquid into the tissue expander. This concerns especially the regions of tissue to be expanded located directly next to the tissue expander. These regions are compressed so much that damage of the tissue occurs. When reducing the amount of liquid that is injected into the tissue expander in each step, problems result from the frequent piercing of the tissue in the region of the valve. Furthermore, the valve may develop a leak, which renders the tissue expander useless. There is no danger for the tissue surrounding the tissue expander as a result of a leaky valve, as long as a physiologically safe, sterile liquid for the filling of the tissue expander.

A self-inflating tissue expander of the type described above is known from the article "A Self-Inflating Tissue Expander" (E. D. Austad et al., Plastic and Reconstructive Surgery, Vol. 70 No. 5, pages 588 ff). This tissue expander consists of a silicone membrane filled with a sodium chloride solution. The molarity of the sodium chloride solution is greater than the physiological molarity of approximately 0.3. The osmotic driving force, which drives body liquid from the tissue surrounding the tissue expander through the semipermeable silicone membrane into the tissue expander, is based on this. The inflation of the tissue expander, and therefore also of the tissue surrounding the tissue expander, occurs without the need of any manipulations from the outside. Furthermore, the tissue surrounding the tissue expander has an exceptional, undamaged quality after the expansion. The reason for this is that the self-inflating tissue expander does not create pressure peaks on the one hand, and that the intake of body fluid into the expander stimulates the metabolism of the surrounding tissue on the other hand. A disadvantage is the small amount of volume expansion of the tissue expander, at least as long as the molarity of the sodium chloride solution initially does not exceed a physiologically acceptable value by far. Another disadvantage is that the properties of the silicone membrane change with the expansion. Especially the pore size of the silicone membrane steadily increases. In this way an increasing amount of sodium chloride ions can pass through the silicone membrane. This leads to a decrease in the osmotic driving force, though, which is not coupled with a gain in the volume expansion of the tissue expander. A further disadvantage of the known tissue expander is the lack of a possibility to influence the direction in which the expansion of the tissue takes place. The form of the silicone membrane has only a minor influence on the shape of the tissue expander after its inflation. It is furthermore established that the inflation of the silicone membrane itself uses up a considerable amount of the osmotic driving force of the tissue expander. This is compounded by the fact that the stretching of the silicone membrane needs more strength as the volume of the tissue expander increases, while the osmotic driving force decreases at the same time. Only a strongly decreasing resulting driving force is then left for the expansion of the tissue surrounding the tissue expander, and the ratio of the initial size of the tissue expander to the attainable final size is further reduced beyond the calculated value.

From the U.S. Pat. No. 4,237,893 a device to widen the cervix is known. The device has a rod-shaped outer form and an at least three layered interior structure. An intermediate layer is made from a hydrophilic polymer material, i. e. a hydrogel. The device is introduced into the cervix and there expands by taking up body fluid from the uterus. By this the cervix is widened in its cross section. When the desired opening of the cervix has taken place after some hours the device is removed and a surgery can be performed through the cervix. The known device serves to temporarily widen an existing orifice of the body, but neither is a new orifice created, nor is additional tissue created. Furthermore, the known device to widen the cervix is not meant to be implanted in the tissue, but to be introduced into an already existing, open body orifice.

The U.S. Pat. No. 3,867,329 describes a method for making a rod-shaped body from hydrogel, which is supposed to serve as a device to widen the cervix. At first a copolymerisation of different aqueous substances is carried out and the resulting copolymer is then further treated. The resulting hydrogels have a swelling coefficient of up to 25 after 5 days in distilled water. Information about a swelling coefficient in a physiological sodium chloride solution is not contained in the U.S. Patent.

From the U.S. Pat. No. 3,975,350 it is known to use a hydrogel made from a polyurethane polymer as an implantable carrier of drugs. The aspect of tissue expansion is not mentioned in the U.S. Patent.

It is known to make so called soft contact lenses from hydrogel. Under the generic term hydrogel polymer substances are understood, which expand in an aqueous environment by taking up water. The amount of expansion is very different, depending on the hydrogel. It is quantified by the swelling coefficient. A swelling coefficient of n means that the initial volume has increased n-fold by taking up water. A constituent of the swelling coefficient is the naming of the solution in which it was determined. It is immediately seen that due to the higher osmotic pressure the swelling coefficient in distilled water will always be larger than in e. g. a physiological sodium chloride solution. The hydrogel from which soft contact lenses are made has a swelling coefficient of less than 4 in a physiological sodium chloride solution. It also has an advantageously high form stability and tear resistance in the swollen state.

SUMMARY OF THE INVENTION

The soft contact lenses "Geaflex 70" from the company "wöhlk-contact-linsen" consist of a copolymer of methylmethacrylate (MMA) and vinylpyrrolidone (VP). It is a solvent-free cross-linked, non-ionic copolymer with free methylene side chains.

It is the object of the invention to provide a self-inflating tissue expander, which in particular allows a directionally controlled expansion of the surrounding tissue on a large scale.

According to the invention this is realised by providing a shaped body of hydrogel. In the simplest embodiment the tissue expander consists exclusively of a shaped body of hydrogel. It is understood that only a hydrogel that retains its shape or at least does not dissolve when taking up water is to be used. Otherwise the removal after the expansion of the tissue would be difficult. A hydrogel that is suitable for the production of the shaped body is the hydrogel from which the known soft contact lenses are made.

An improved swelling capability is obtained when the hydrogel is an ionic hydrogel. The osmolarity of the hydrogel is increased by the ion-anion-dissociation of the hydrogel in aqueous solution.

Especially well suited as constituents of tissue expanders are ionic hydrogels that are formed on the basis of a fully cross-linked, non-ionic polymer. In this way the ionic hydrogel has the mechanical stability of a non-ionic polymer, but at the same time a significantly higher swelling coefficient as compared to non-ionic hydrogels. An ionic hydrogel is obtained in a comparatively easy way when a non-ionic hydrogel is saponified.

The saponifiable non-ionic hydrogel may be a polymer on the basis of methylmethacrylate (MMA). Such polymers have methylene side chains that are transformed into carboxyl side chains under the influence of soda lye and under the separation of methylene. In an aqueous solution the carboxyl groups dissociate into negatively charged $CO_2^-$-groups and free $H^+$-ions.

The shaped body may be surrounded by a selectively permeable membrane. In this way hydrogels can be used that grow to 20 times their initial volume taking up water in physiological solutions. The accompanying dissolving of the hydrogel happens only inside the selectively permeable membrane. It is understood that the selectively permeable membrane should essentially be permeable for water. For this reason semi-permeable membranes are suited for the tissue expander. But also selectively permeable membranes which next to water are permeable for small ions may advantageously be applied. In any case lies the cut-off limit of the selectively permeable membrane below approximately 4 micrometers, so that blood cells are effectively held back.

The selectively permeable membrane may be stretch resistant. By this the shape of the inflated tissue expander may be predetermined by the design of the membrane.

It is of advantage to pre-wet the membrane. It is necessary to condition the selectively permeable membrane prior to the application of the tissue expander, so that sufficient permeation rates are obtained from the beginning on. When the conditioning is performed by the tissue surrounding the tissue expander a lot of time is lost. So it is sensible to bring the membrane to a moisture level that ensures the desired function before the implantation of the tissue expander.

An aqueous solution may be provided inside the membrane. The aqueous solution ensures that all surfaces of the shaped body are wetted and therefore available for the taking up of water and the expansion of the hydrogel.

Sodium chloride or some other physiologically tolerated salt may be dissolved in the solution. The salt helps to create a further osmotic driving force which acts between the tissue surrounding the tissue expander and the solution. This force itself also leads to an expansion of the tissue expander, but mainly serves to provide a sufficient amount of water for the expansion of the hydrogel. Furthermore, the salt can be used to specifically exploit certain properties of some hydrogels. These hydrogels can take up water only when the concentration of salt in their vicinity does not exceed a certain value. Conversely they ensure by taking up water that the concentration of salt in their vicinity does not fall below a certain value. By this the osmotic driving force between the tissue surrounding the tissue expander and the solution is always maintained so far that water enters the tissue expander, by which the hydrogel itself ultimately ensures its supply with water.

Instead of or additionally to the salt, macromolecules with especially polyelectrolytic properties may be dissolved in the solution. Macromolecules such as protein or carbohydrate molecules even cannot pass through selectively permeable membranes that have high permeation rates for water and are transmissiable for sodium chloride ions. By virtue of this property they are permanently available to keep up the osmotic driving force. Polyelectrolytic properties of the macromolecules support the purely osmotic driving force by additional electrochemical effects.

The solution may be approximately unimolar. This value refers to the initial concentration of the solution. It ensures that the volume occupied by the solution at time of the implantation of the tissue expander is small at first, but that the wetting of the shaped body is ensured even after its swelling. A unimolar sodium chloride solution is not physiologically tolerable, as a skilled person will immediately see. The molarity of one should therefore be attained through the use of different dissolved substances, especially proteins.

The shaped body of hydrogel may be separated into a number of individual bodies. The time it takes for the hydrogel to obtain its maximum expansion is primarily determined by the dimensions of the shaped body. This means that the speed of the expansion of the shaped body may be accelerated by the separation into individual bodies. On the one hand the distance the water has to go through the hydrogel is limited and on the other hand a larger surface area for the entry of the water into the hydrogel is provided.

A gas-filled pressure buffer may be provided in the tissue expander. Gas-filled pressure buffers are extremely well suited to neutralize pressure peaks. Actually, pressure peaks do not occur with the new tissue expander as opposed to non self-inflating tissue expanders, but the pressure exerted by the tissue expander on the surrounding tissue may be distributed more evenly by the insertion of the pressure buffer. Carbon dioxide is especially suited as a filling gas, since it is resorbed by the surrounding tissue when released. The pressure buffer may be arranged at any place inside the tissue expander, e. g. inside the shaped body of hydrogel or next to the shaped body in the membrane enclosing the shaped body.

The shaped body or the individual bodies of hydrogel and/or the membrane may be partially vapour-coated with a metal, especially a noble metal. By the partial vapour-coating with metal the active surface area of the shaped body or the individual bodies is reduced. This also reduces their swelling speed. This is sensible when, for instance, an especially slow expansion of tissue by the tissue expander is to be attained.

BRIEF DESCRIPTION OF THE DRAWINGS

The invention is further explained and described with the aid of two preferred embodiments. The Figures show.

DETAILED DESCRIPTION

Figure 1:
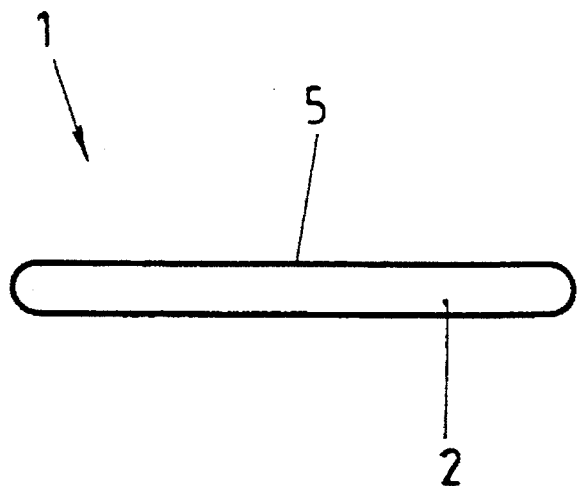
FIG. 1 illustrates a first embodiment of the self-inflating tissue expander.

The approximately rod-shaped tissue expander 1 shown in FIG. 1 is intended for the expansion of the periosteum. More specifically it is intended for the expansion of the periosteum of the upper side of a jawbone crest, until enough material to form new bone matter to build up a raised jawbone crest can be brought into the pocket in the periosteum thus created. The raising of the jawbone crest often is a prerequisite for the sensible employment of tooth prostheses with patients that have been without teeth for a long time. The tissue expander 1 consists exclusively of a shaped body 5 made of hydrogel 2. The hydrogel is rigid in a dry state before the implantation, so that it may easily be inserted into a pocket between the jawbone crest and the lifted periosteum. The hydrogel 2 is based on a copolymer of methylmethacrylate (MMA) and vinyl pyrrolidone (VP). The hydrogel 2 further contains additives, with which a good mechanical and form stability of the tissue expander is obtained. The hydrogel 2 is of identical composition as the hydrogel used for the manufacturing of the soft contact lenses "Geaflex 70" by the company "wöhlk-contact-linsen". The physiological tolerability of this hydrogel has been proven to a large degree. In a physiological sodium chloride solution the hydrogel swells by taking up water until 3.6 times the initial volume is obtained. For this approximately 220% of the starting weight of the hydrogel is absorbed in the form of water. The driving force of this taking up of water is of osmotic nature, with the surface of the hydrogel acting as a membrane. The tissue expander 1 reaches a similar degree of swelling in surrounding human tissue as does the hydrogel 1 in a physiological sodium chloride solution, since all human body fluids are in a quite precise osmotic equilibrium with a physiological sodium chloride solution. Reductions have to be taken into consideration for the resistance the expanding tissue, in this case the periosteum, puts against its stretching by the tissue expander 1. In the case of the expansion of periosteum a swelling by a factor of three with respect to the initial volume in the tissue is sufficient, though. It is especially advantageous that the shaped body 5 of the tissue expander 1 even in the swollen state remains a single, tear resistant piece of hydrogel and that is does not show any signs of deterioration. This makes the explantation of the tissue expander much easier. After the explantation it is to be noted that the periosteum expanded by the tissue expander has a very good constitution, since it was exposed to a constant metabolism just by the taking up of water by the tissue expander. The bone forming matter put under the periosteum to build up the jawbone crest are thus converted to bone substance more quickly.

Figure 2:
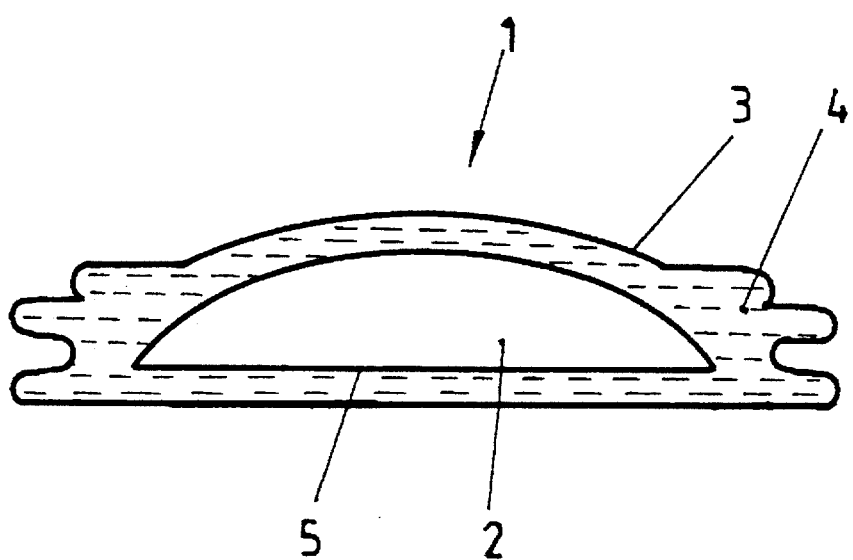
FIG. 2 illustrates a second embodiment of the self-inflating tissue expander.

In some cases the degree of expansion by a factor of three with respect to the initial volume, which can be obtained with the tissue expander according to FIG. 1, is not sufficient. For these cases the tissue expander 1 according to FIG. 2 is provided. Here the tissue expander 1 has a shaped body 5 of hydrogel 2 inside of a closed membrane 3. The composition of the hydrogel is chosen so that it loses its form stability and also its mechanical stability in the swollen state, but that it reaches a final volume up to 20 times the initial volume. The explantability of the tissue expander 1 according to FIG. 2 therefore is based on the membrane 3 surrounding the hydrogel 2. The membrane 3 is formed to be selectively permeable and allows an unhindered passage of water from the tissue surrounding the tissue expander 1 to the hydrogel 2, while it is impenetrable for larger molecules. The "NADIR"-membranes of the company "Hoechst AG", for instance, which are based on cellulose, cellulose acetate or polyamide, and which are stabilized by a comparatively large pored support membrane made of polypropylene, are suitable as material for the membrane 3. The design of the membrane 3 determines the shape of the tissue expander 1 after its inflation. The membrane 3 has to be conditioned, i. e. wetted, before the tissue expander 1 is implanted, so that it has a high rate of permeation for water from the surrounding tissue from the beginning on. In order to ensure the taking up of water by the hydrogel 2 from the beginning, an aqueous solution 4 is provided inside the tissue expander 1 already before the implantation. The solution 4 is in contact with the inside surface of the membrane 3 and fully wets the surface of the tissue expander 1. It serves as a mediator between the hydrogel 2 and the membrane 3 or the tissue surrounding the tissue expander 1. The solution 4 itself should have an osmotically acting concentration with respect to the surrounding tissue. This ensures that the volume of the solution 4 increases, so that the hydrogel 2 is fully wetted by the solution 4, even when swollen to a high degree. Sodium chloride or also physiologically tolerable macromolecules are suitable as additives to the solution 4. The latter are retained especially easily in the tissue expander by membranes which have very high permeation rates for water and therefore also let sodium chloride pass in a certain amount. The tissue expander presented here is suited, for instance, to create a cavity for a silicone implant to construct an artificial breast.

Figure 3:
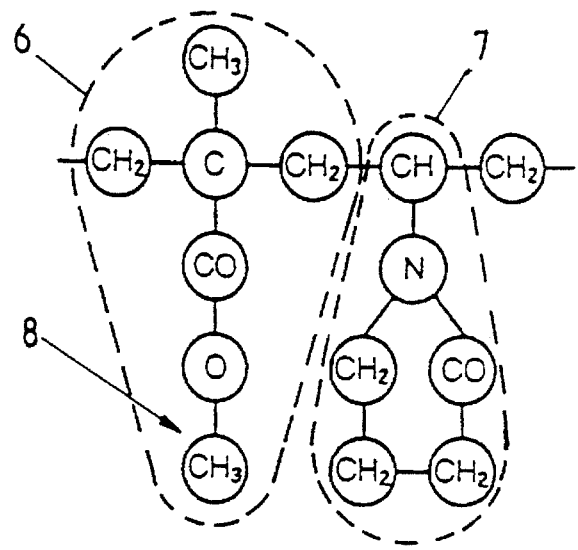
FIG. 3 illustrates a structural formula of the tissue expander according to FIG. 1.
Figure 4:
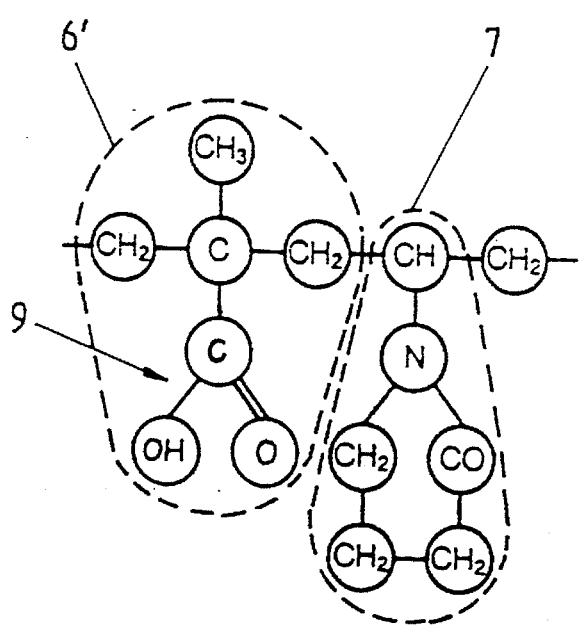
FIG. 4 illustrates a structural formula of a further embodiment of the tissue expander.

Apart from the fashioning of the tissue expander according to FIG. 2 there is a further possibility to increase the swelling cofficient of the tissue expander of hydrogel according to FIG. 1. This possibility is explained with the aid of FIGS. 3 and 4, where FIG. 3 is the structure formula of the hydrogel 2 of the shaped body 5 according to FIG. 1 and FIG. 4 is the structure formula of a further, not separately shown shaped body of a further embodiment of the tissue expander. As described above, the hydrogel 2 of the shaped body 5 according to FIG. 1 is a copolymer of methylmethacrylate (MMA) 6 and vinyl pyrrolidone (VP) 7. The structure has free methylene side chains 8, as shown in FIG. 3. When the structure is saponified with soda lye according to FIG. 3, the structure according to FIG. 4 is produced by the separation of methylene. Here there is a free carboxyl group 9 in the vicinity of the methacryl group 6' instead of the methyl group 8. The carboxyl group dissociates in an aqueous solution into a negatively charged rest $CO_2^-$ and a free ion $H^+$. In this way the osmolarity of the hydrogel 2 is increased by saponifying. A hydrogel with the structure formula according to FIG. 4 has a swelling coefficient of more than 30 in distilled water and of approximately 10 to 12 in a physiological sodium chloride solution. Even so, the mechanical stability after the saturation of the hydrogel with water is still good. The reason for this is that the basic structure responsible for the mechanical properties has not been changed by the saponification.

In the following a method is described, with which the copolymer of methylmethacrylate (MMA) and vinyl pyrrolidone (VP) of the tissue expander according to FIG. 1 has been successfully treated, in order to significantly improve its swelling properties. The following numbers refer to compact pieces of polymer approximately 1 cm³ in size. The stated times are to be increased for larger pieces of polymer due to the longer diffusion times and they are to be decreased for smaller pieces or pieces with a large relative surface area. At first the copolymer is saponified with a unimolar soda lye for five days. It is then washed in distilled water, which is renewed a number of times, for 30 days, in order to remove rests of the soda lye from the copolymer. Already after the saponification does the copolymer have the structure shown in FIG. 4. After the washing the copolymer is brought into equilibrium in sodium chloride solutions with ascending concentrations. This causes an osmotic shrinking of the copolymer previously saturated with distilled water. Suitable are concentrations of the sodium chloride solution beginning with 0.1%, ascending over 0.3% and 0.5% to 0.9%. This bringing into an equilibrium is done in the respective solution for a duration of 1 to 3 days. The final value of the concentration of the sodium chloride solution of 0.9% corresponds to a physiological sodium chloride solution. The not fully dehydrated copolymer is put into a germ proof but steam transmitting enclosure and sterilized therein for 10 minutes at 120° C. in an autoclave. Finally there is a curing at room temperature and reduced humudity, in order to reduce the water content of the copolymer so far that it is nearly water free. The copolymer removed from the germ proof enclosure has a swelling coefficient of 12 in a physiological sodium chloride solution.

In a variation of the prescribed method the copolymer is additionally brought into equilibrium with a sodium chloride solution which has a concentration that is higher than that of a physiological solution and which e.g. has a concentration of 1.2%. This causes a higher degree of saturation of the carboxyl groups 9 of the copolymer ionized by dissociation, with the aid of $Na^+$-ions dissociated in the sodium chloride solution. This results in quasi-non-ionic properties; of the dehydrated hydrogel during the renewed taking up of water, until the $Na^+$-ions have diffused out of the copolymer. The initial reduction in the swelling speed accompanying this is advantageous, since it especially prevents excessive strain of the tissue surrounding the tissue expander after the implantation.

While the foregoing specification and drawings disclose preferred embodiments of the invention, it will be understood by those skilled in the art that variations and modifications thereof can be made without departing from the spirit and scope of the invention as set forth in the following claims.

I claim:

1. A tissue expander for creating cavities for the insertion of implants or to provide tissue for a self transplantation comprising a hydrogel having a shaped body with a surface, said surface acting as a membrane disposed therearound, said hydrogel being capable of inflating due to an osmotic driving force of said hydrogel, a second selectively permeable membrane disposed around said first mentioned membrane and defining a space therebetween, and an aqueous solution disposed in said space between said membranes and generating an osmotic driving force for inflating the tissue expander.

2. A tissue expander as defined in claim 1, wherein said hydrogel is an ionic hydrogel.

3. A tissue expander as defined in claim 1, wherein said hydrogel is a saponified non-ionic hydrogel.

4. A tissue expander as defined in claim 1, wherein said hydrogel is non-ionic and is a polymer on the basis of methylmethacrylate (MMA).

5. A tissue expander as defined in claim 1, in which said aqueous solution has a molarity of approximately 1.

6. A tissue expander as defined in claim 1, in which sodium chloride, another physiologically tolerated salt, or a macromolecule with polyelectrolytic properties is dissolved in said solution.

\* \* \* \* \*